US00PP21599P2

(12) United States Plant Patent
Hanes

(10) Patent No.: US PP21,599 P2
(45) Date of Patent: Dec. 28, 2010

(54) ***PETUNIA* PLANT NAMED 'PIC ROSSA'**

(50) Latin Name: *Petunia hybrida*
Varietal Denomination: Pic Rossa

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/653,300

(22) Filed: Dec. 11, 2009

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L Bell
(74) *Attorney, Agent, or Firm*—S. Matthew Edwards

(57) ABSTRACT

A new *Petunia* plant named 'Pic Rossa' particularly distinguished by the small red-purple flowers, early blooming, good floriferiousness, and initially semi-compact and then an outwardly spreading plant habit.

1 Drawing Sheet

Latin name of the genus and species of the plant claimed: *Petunia hybrida.*

Varietal denomination: 'Pic Rossa'.

BACKGROUND OF THE NEW PLANT

The present invention comprises a new *Petunia*, botanically known as *Petunia hybrida*, and hereinafter referred to by the variety name 'Pic Rossa'.

'Pic Rossa' is a product of a planned breeding program. The new cultivar has small red-purple flowers, early blooming, good floriferousness, and initially semi-compact and then an outwardly spreading plant habit.

'Pic Rossa' originated from a hybridization made in August 2004 in a controlled breeding environment in Gilroy, Calif. The seed was sown in February 2005. The female parent was the proprietary plant designated '1356-6' (unpatented) with larger rose colored flowers and a more trailing habit.

The male parent of 'Pic Rossa' was a commercial variety identified as 'MP209,' U.S. Plant Pat. No. 16,439, with larger rose colored flowers with a deeper colored throat, and is earlier to flower.

'Pic Rossa' was selected as one flowering plant within the progeny of the stated cross in a controlled environment in May 2005 in Gilroy, Calif.

The first act of asexual reproduction of 'Pic Rossa' was accomplished when vegetative cuttings were propagated from the initial selection in May 2005 in a controlled environment in Gilroy, Calif.

BRIEF SUMMARY OF INVENTION

Horticultural examination of plants grown from cuttings of the plant initiated in May 2005, and continuing thereafter, has demonstrated that the combination of characteristics as herein disclosed for 'Pic Rossa' are firmly fixed and are retained through successive generations of asexual reproduction.

'Pic Rossa' has not been observed under all possible environmental conditions. The phenotype may vary significantly with variations in environment such as temperature, light intensity and day length.

A Plant Breeder's Right for this cultivar was applied for in Canada on Jan. 30, 2009. 'Pic Rossa' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Pic Rossa' with colors being as true as possible with an illustration of this type.

Figure 1:
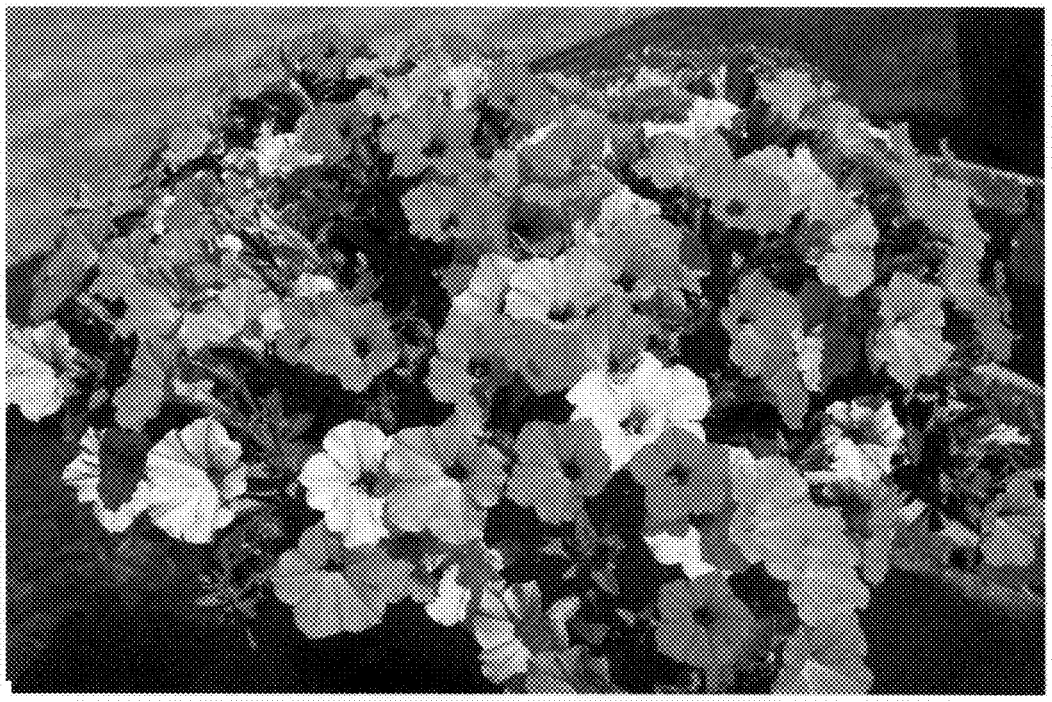
Figure 2:
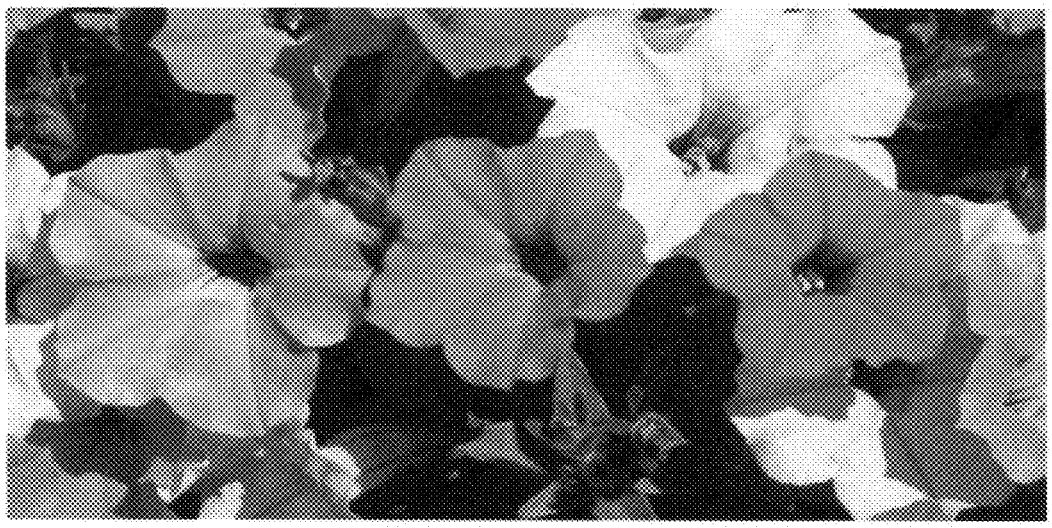

The photographic drawing shows in FIG. 1, three flowering potted plants of the new variety, and in FIG. 2, a close-up of the flowers.

DETAILED BOTANICAL DESCRIPTION

The plant descriptions, measurements and aforementioned photographs were taken in Gilroy, Calif. from plants growing outside in 10 inch basket trials, 3 plants per basket. These plants were approximately 14-16 weeks of age.

Color references are made to The Royal Horticultural Society Colour Chart (R.H.S.) 2001.

TABLE 1

DIFFERENCES BETWEEN THE NEW VARIETY 'PIC ROSSA' AND THE MOST RESEMBLING VARIETY 'MP209' (U.S. Plant Pat. No. 16,439)

| | 'Pic Rossa' | 'MP209' (U.S. Plant Pat. No. 16,439) |
|---|---|---|
| Flower size: | Smaller | Larger |
| Throat coloring: | More conspicuous | Less conspicuous |
| Flowering response: | Later | Earlier |

Plant:

*Form, growth and habit.*—Initially semi-compact to outwardly spreading, strong vigorous habit, well branched, small foliage, early and continuous flowering.

*Plant height.*—18-21 cm.
*Plant height (inflorescence included).*—21-25 cm.
*Plant width.*—40-45 cm.
*Garden performance and tolerance to weather.*—Very good.
*Crop time to flowering.*—About 8-9 weeks.

Roots:
*Number of days to initiate roots and produce a rooted cutting.*—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—Little lighter than RHS 137B.
*Immature, leaf color, lower surface.*—Closest to RHS 137C.
*Mature, leaf color, upper surface.*—RHS 137B.
*Mature, leaf color, lower surface.*—Closest to RHS 137C.
*Length.*—2.6-2.9 cm.
*Width.*—1.2-1.5 cm.
*Shape.*—Ovate.
*Base shape.*—Attenuate.
*Apex shape.*—Acute.
*Margin.*—Entire.
*Texture, upper surface.*—Glandular hairs.
*Texture, lower surface.*—Glandular hairs.
*Color of veins, upper surface.*—RHS 144A basally, otherwise indistinct.
*Color of veins, lower surface.*—RHS 144A.
*Petiole color.*—Little darker than RHS 144A.
*Length.*—0.5 cm.
*Diameter.*—0.15-0.2 cm.
*Texture.*—Glandular hairs of various lengths.

Stem:
*Color of stem.*—Closest to RHS 144A.
*Length of stem.*—About 30.0 cm.
*Diameter.*—0.2-0.25 cm.
*Length of internodes.*—1.0-1.3 cm.
*Texture.*—Glandular hairs.
*Color of peduncle.*—Closest to RHS 144A.
*Length of peduncle.*—1.6-2.0 cm.
*Peduncle diameter.*—0.15 cm.
*Texture.*—Glandular hairs.

Inflorescence:
*Type.*—Flowers appear solitary in upper leaf axis.
*Floret type.*—Funnel-shaped; 5 lobed petals; fused at the base; calyx, 5 deeply lobed sepals.
*Blooming habit.*—Continuous throughout the growing season; Good floriferousness.
*Quantity of inflorescences per plant.*—About 35-45.
*Lastingness of individual blooms on the plant.*—About 4-8 days.
*Fragrance.*—Slightly sweet and spicy.

Bud (just before opening/showing color):
*Color.*—RHS N66A but with a little more purple.
*Length.*—2.4-2.9 cm.
*Width.*—0.4 cm.
*Shape.*—Oblong.

Immature inflorescence:
*Diameter.*—2.7-2.9 cm.
*Color, upper surface.*—Closest to RHS N66A but with a little more purple.
*Color, lower surface.*—RHS N66D.

Mature inflorescence:
*Floret horizontal diameter.*—3.0-3.4 cm.
*Vertical depth.*—3.3-3.5 cm.
*Petal color, upper surface.*—Closest to N66B but with a little more purple, with RHS 67A mid veins; maturing to shades of RHS 67A to RHS 67C; and finally fading to shades of white with various hues and mottling of about RHS N66C, RHS N66D and RHS 68B.
*Petal color, lower surface.*—About N66D fading to N155B.
*Petal apex shape.*—Cuspidate.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Few glandular hairs mainly on the veins.
*Corolla tube color inside.*—RHS N155B ground color with veins of about RHS N186C in varying shades.
*Outside.*—RHS N155B with veins of RHS N77A.
*Corolla tube length.*—2.2-2.5 cm.
*Corolla texture.*—Short hirsute along the veins.

Calyx:
*Color, upper surface.*—Lighter than RHS 137B.
*Color, lower surface.*—Lighter than RHS 137B.
*Length.*—1.0-1.2 cm.
*Width.*—0.15-0.2 cm.
*Shape.*—Ligulate.
*Apex shape.*—Acute.
*Based.*—Fused.
*Margins.*—Entire.
*Texture, upper surface.*—Glandular hairs of various lengths.
*Texture, lower surface.*—Glandular hairs of various lengths.

Reproductive organs:
*Pistil.*—1.
*Length.*—1.8 cm.
*Style color.*—Closest to RHS N155D.
*Style length.*—1.5-1.6 cm.
*Stigma color.*—RHS 144A.
*Ovary color.*—Not observed.
*Stamens.*—5.
*Color of filaments.*—Closest to RHS N 155D.
*Length filaments.*—1.5 cm.
*Anther color.*—RHS N155D with a hint of purple.
*Anther length.*—About 0.2 cm.
*Anther shape.*—Reniform.
*Color of pollen.*—RHS 155D.
*Pollen amount.*—Moderate.
*Fertility/seed set.*—Has not been observed on this hybrid.

Disease/pest resistance: Has not been observed on this hybrid.

What is claimed is:

1. A new and distinct variety of *Petunia* plant named 'Pic Rossa,' substantially as illustrated and described herein.

* * * * *